United States Patent
Sakagawa (10) Patent No.: US 9,962,073 B2
(45) Date of Patent: May 8, 2018

(54) TOMOGRAPHIC IMAGE CAPTURING APPARATUS, METHOD FOR CAPTURING TOMOGRAPHIC IMAGE, PROGRAM, AND STORAGE MEDIUM

(71) Applicant: CANON KABUSHIKI KAISHA, Tokyo (JP)

(72) Inventor: Yukio Sakagawa, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 4 days.

(21) Appl. No.: 15/089,086

(22) Filed: Apr. 1, 2016

(65) Prior Publication Data
US 2016/0213245 A1    Jul. 28, 2016

Related U.S. Application Data

(63) Continuation of application No. 12/903,963, filed on Oct. 13, 2010, now Pat. No. 9,326,676.

(30) Foreign Application Priority Data

Oct. 19, 2009 (JP) ................. 2009-240865

(51) Int. Cl.
*A61B 3/14* (2006.01)
*A61B 3/00* (2006.01)
*A61B 3/10* (2006.01)

(52) U.S. Cl.
CPC ............ *A61B 3/0091* (2013.01); *A61B 3/102* (2013.01)

(58) Field of Classification Search
CPC ......... A61B 3/103; A61B 3/02; A61B 3/1015; A61B 3/14; A61B 3/12; A61B 3/156
USPC .......................... 351/200, 205, 206, 207, 246
See application file for complete search history.

(56) References Cited

U.S. PATENT DOCUMENTS

2008/0030680 A1* 2/2008 Tsukada ................. A61B 3/102
351/206

* cited by examiner

*Primary Examiner* — James Greece
(74) *Attorney, Agent, or Firm* — Canon U.S.A., Inc. IP Division (57) ABSTRACT

A tomographic image capturing apparatus includes a fixation lamp configured to guide a line of sight of a subject's eye, and a control unit configured to control a projection position of measuring light according to a predetermined position on a fundus of the subject's eye and a projection position of the fixation lamp.

13 Claims, 10 Drawing Sheets

| FIXATION LAMP TURN-ON POSITION (Y POSITION) | FIXATION LAMP PROJECTION ANGLE 405 (Y DIRECTION) |
|---|---|
| 8 | 14° |
| 7 | 10° |
| 6 | 6° |
| 5 | 2° |
| 4 | −2° |
| 3 | −6° |
| 2 | −10° |
| 1 | −14° |

FIG. 6

TOMOGRAPHIC IMAGE CAPTURING APPARATUS, METHOD FOR CAPTURING TOMOGRAPHIC IMAGE, PROGRAM, AND STORAGE MEDIUM

CROSS-REFERENCE TO RELATED APPLICATIONS

This application is a Continuation, and claims the benefit, of U.S. patent application Ser. No. 12/903,963 filed Oct. 13, 2010 (now U.S. Pat. No. 9,326,676), which claims priority from Japanese Patent Application No. 2009-240865 filed Oct. 19, 2009. Each of U.S. patent application Ser. No. 12/903,963 and Japanese Patent Application No. 2009-240865 is hereby incorporated by reference herein in its entirety.

BACKGROUND OF THE INVENTION

Field of the Invention

The present invention relates to a tomographic image capturing apparatus for capturing a tomographic image of a subject's eye by setting a turn-on position of a fixation lamp for fixing the line of sight of the subject's eye and an imaging position on the retina, a method for capturing a tomographic image, a program therefor, and a storage medium.

Description of the Related Art

An optical coherence tomography (OCT) for ophthalmology can be used to three-dimensionally observe the state of the inside of the layer of the retina. The OCT is useful for more exact disease diagnosis and, therefore, used by many ophthalmologists.

In image capturing by using the OCT, a fixation lamp is turned on and a predetermined position on the fundus is guided to the vicinity of the optical axis of the optical system of the OCT (refer to Japanese Patent Application Laid-Open No. 2007-275374).

However, the technique discussed in Japanese Patent Application Laid-Open No. 2007-275374 discloses no concept of adjusting the position of measuring light for optical interference on the fundus with the predetermined position thereof.

Therefore, it is necessary to guide a desired position on the fundus to the vicinity of the optical axis of the OCT by using a fixation lamp. Therefore, with a large interval of fixation lamp turn-on positions, it may become difficult to guide the predetermined position on the fundus to the vicinity of the optical axis of the optical system of the OCT.

SUMMARY OF THE INVENTION

According to an aspect of the present invention, a tomographic image capturing apparatus includes a fixation lamp configured to guide a line of sight of a subject's eye, and a control unit configured to control a projection position of measuring light according to a predetermined position on a fundus of the subject's eye and a projection position of the fixation lamp.

According to another aspect of the present invention, a tomographic image capturing apparatus includes a light source configured to generate measuring light, a scanning unit configured to scan a subject's eye with the measuring light, a detection unit configured to detect composite light obtained by combining return light acquired by scanning with the measuring light by the scanning unit with reference light, a specification unit configured to specify a predetermined position on a fundus of the subject's eye, a fixation lamp configured to guide a line of sight of the subject's eye, and a control unit configured to control the scanning unit according to the predetermined position on the fundus and a projection position of the fixation lamp on the fundus.

According to yet another aspect of the present invention, a method for capturing a tomographic image includes turning on a fixation lamp configured to guide a line of sight of a subject's eye, and controlling a projection position of measuring light according to a predetermined position on a fundus of the subject's eye and a projection position of the fixation lamp.

According an exemplary embodiment of the present invention, in capturing a tomographic image by using an OCT, it becomes easier to set a fixation lamp turn-on position and a scanning position.

Further features and aspects of the present invention will become apparent from the following detailed description of exemplary embodiments with reference to the attached drawings.

BRIEF DESCRIPTION OF THE DRAWINGS

The accompanying drawings, which are incorporated in and constitute a part of the specification, illustrate exemplary embodiments, features, and aspects of the invention and, together with the description, serve to explain the principles of the invention.

DESCRIPTION OF THE EMBODIMENTS

Various exemplary embodiments, features, and aspects of the invention will be described in detail below with reference to the drawings.

A tomographic image capturing apparatus 10 according to an exemplary embodiment of the present invention displays to an operator a current fundus image of an object under measurement. Then, the tomographic image capturing apparatus 10 controls a fixation lamp turn-on position according to a position on the fundus image specified by the operator and a measuring light projection position on the fundus. Further, the tomographic image capturing apparatus 10 controls a scanning position so that the measuring light projection position on the retina (fundus) is scanned by the measuring light.

Figure 1:
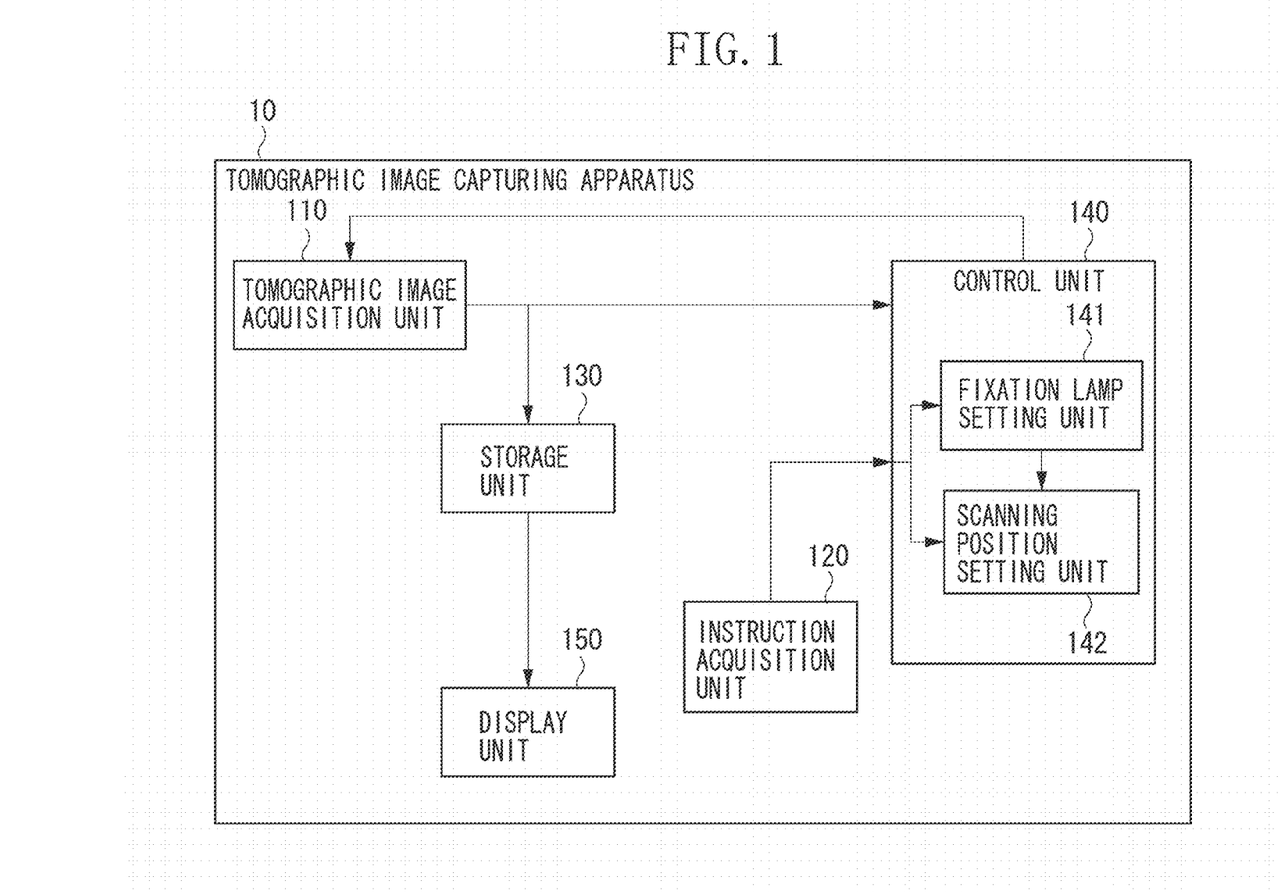
FIG. 1 illustrates a functional configuration of a tomographic image capturing apparatus according to a first exemplary embodiment of the present invention.

FIG. 1 is a functional block diagram of the tomographic image capturing apparatus 10 according to the first exemplary embodiment of the present invention. The tomographic image capturing apparatus 10 includes a tomographic image acquisition unit 110, an instruction acquisition unit 120, a storage unit 130, a control unit 140, and a display unit 150.

The tomographic image acquisition unit 110 deflects the measuring light to scan the measuring light projection position on the retina (also referred to as fundus) of a subject's eye. Then, the tomographic image acquisition unit 110 detects composite light obtained by combining return light from the retina with reference light to acquire a tomographic image of the retina.

The instruction acquisition unit 120 acquires an imaging position instruction from an operator (not illustrated). The storage unit 130 stores tomographic images of the subject's eye and image capturing control parameters used for tomographic image capturing.

The control unit 140, having a central processing unit (CPU) for control, includes a fixation lamp setting unit 141 and a scanning position setting unit 142. The control unit 140 sets parameters for tomographic image capturing, such as the fixation lamp turn-on position, the scanning position and scanning speed of the measuring light, etc., to control image capturing.

The control unit 140 stores a computer program for controlling the CPU (computer) and includes work memory (not illustrated) to control the entire image capturing operation of the tomographic image capturing apparatus 10 according to the computer program. This computer program can be installed by using a storage medium (not illustrated).

The display unit 150 displays a tomographic image and a fundus image of the subject's eye, and image capturing control parameters.

Figure 2:
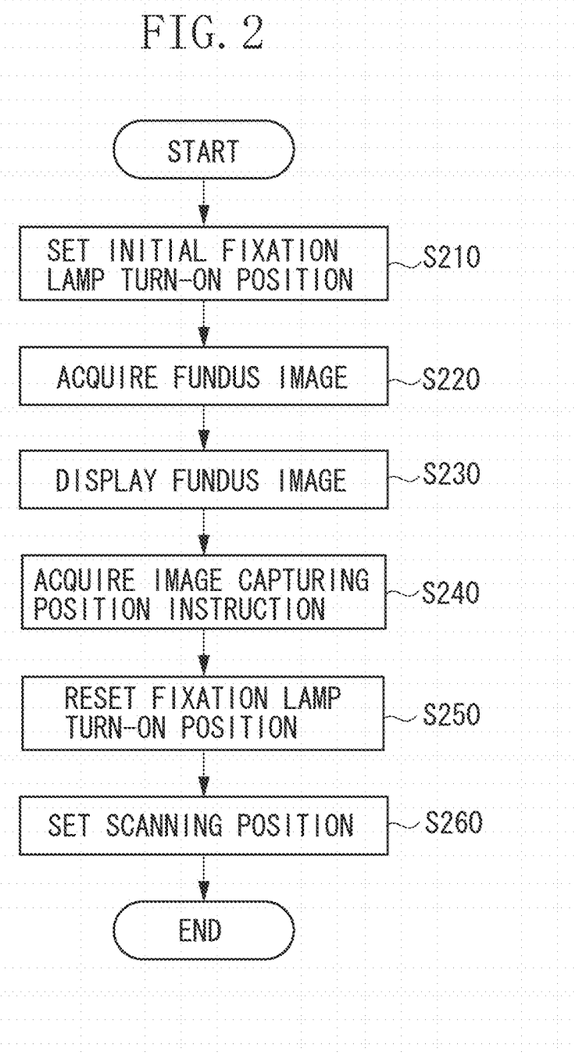
FIG. 2 is a flow chart illustrating processing performed by the tomographic image capturing apparatus according to the first exemplary embodiment.

Processing performed by the control unit 140 to control the tomographic image capturing apparatus 10 will be described below with reference to the flow chart in FIG. 2.

In step S210, the fixation lamp setting unit 141 sets an initial fixation lamp turn-on position.

Although the fixation lamp turn-on position is set to a predetermined fixation lamp turn-on position, it may be set to an initial fixation lamp turn-on position specified by the operator.

In step S210, the control unit 140 sets other parameters (scanning speed, acquisition rate, etc.) necessary for tomographic image capturing.

The control unit 140 transmits the initial fixation lamp turn-on position and the tomographic image capturing parameters to the storage unit 130 for storage.

In step S220, the tomographic image acquisition unit 110 acquires a fundus image at the fixation lamp turn-on position set in step S210. Acquisition of a fundus image from a wide-range 3D tomographic image will be described below.

The tomographic image acquisition unit 110 includes a Fourier-domain-based OCT according to the present exemplary embodiment.

Figure 3A:
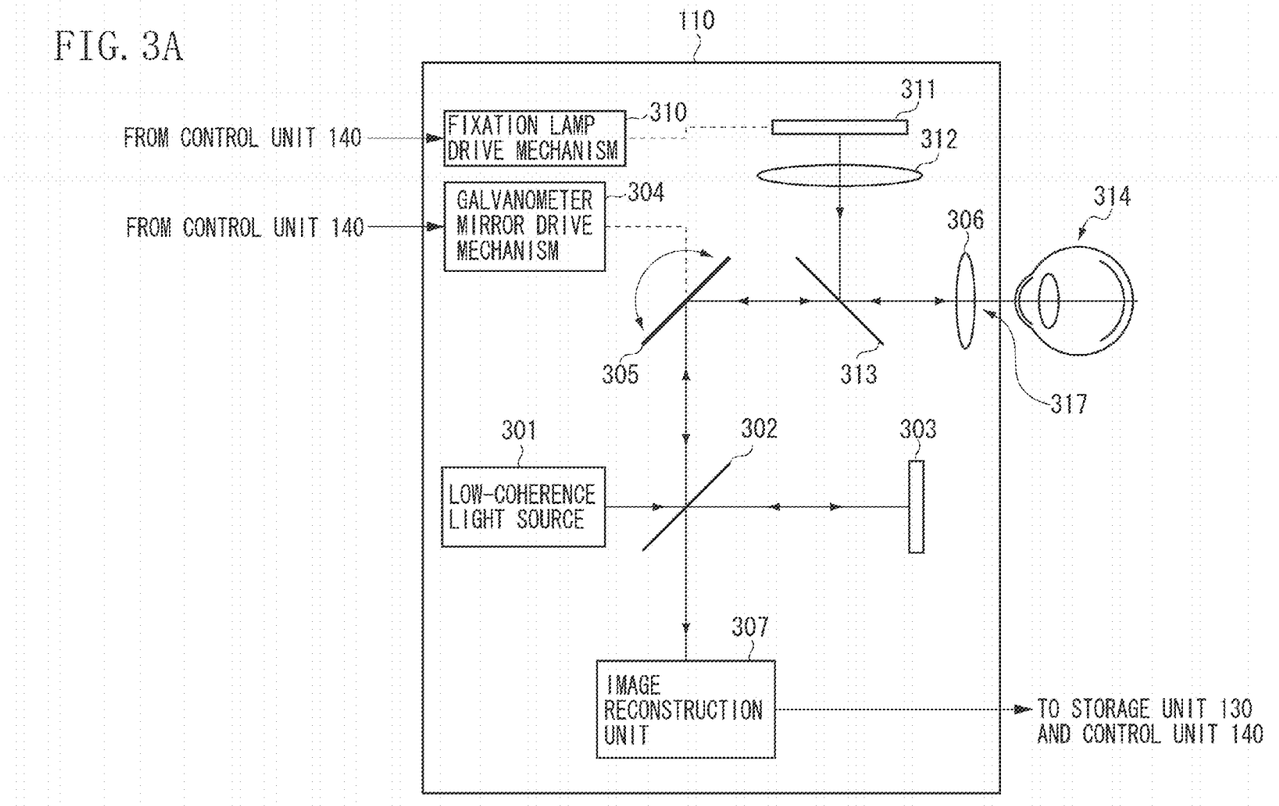
FIGS. 3A and 3B illustrate a functional configuration of a tomographic image acquisition unit according to the first exemplary embodiment.
Figure 3B:
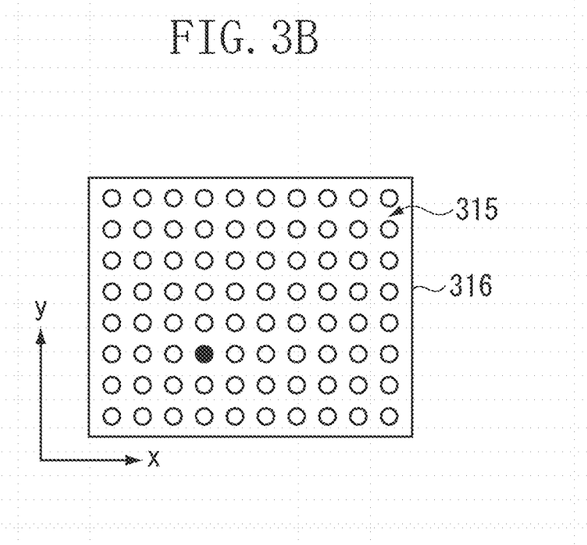

FIGS. 3A and 3B illustrate a functional configuration of the tomographic image acquisition unit 110. A fixation lamp drive mechanism 310 turns on a specified position on a fixation lamp 311 according to the fixation lamp turn-on position transmitted from the control unit 140 to the tomographic image acquisition unit 110.

Light from the fixation lamp 311 passes through a lens 312, a half mirror 313, and an objective lens 306, and then is projected onto the retina of the subject's eye 314. Further, the control unit 140 controls a galvanometer mirror drive mechanism 304 according to the transmitted scanning position. The galvanometer mirror drive mechanism 304 drives a galvanometer mirror 305.

The galvanometer mirror 305 is composed of two mirrors (not illustrated) capable of main and sub scanning. A low-coherence light source 301 generates a low-coherence light beam as measuring light. This light beam is split into measuring light and reference light by a half mirror 302. The measuring light advances to the subject's eye 314 via the objective lens 306, and the reference light advances to a reference mirror 303.

Then, the measuring light and the reference light reflected by the subject's eye 314 and the reference mirror 303, respectively, are combined into interference light. An image reconstruction unit 307 receives the interference light to reconstruct a tomographic image of the retina (also referred to as fundus) from the interference light.

The image reconstruction unit 307 transmits the reconstructed tomographic image to the storage unit 130 and the control unit 140. Referring to FIG. 3A, the objective lens 306 has an optical axis 317.

The tomographic image acquisition unit 110 performs main scanning at a plurality of sub scanning positions on the retina to acquire 2D tomographic images. The tomographic image acquisition unit 110 also performs main and sub scanning with a wide viewing angle to acquire a wide-range 3D tomographic image.

Further, the tomographic image acquisition unit 110 generates a projection image having tomographic images integrated in the depth direction (Z-axis direction) by using the wide-range 3D tomographic image to generate a fundus image.

The fundus image acquired in step S220 is transmitted to the storage unit 130 and the display unit 150.

The tomographic image acquisition apparatus 110 may instead be provided with a scanning laser ophthalmoscope (SLO) or an infrared camera to capture a 2D fundus image.

In step S230, the display unit 150 displays to the operator the fundus image acquired in step S220.

In step S240, the instruction acquisition unit 120 acquires an imaging position instruction from the operator. The operator selects a predetermined position in the fundus image displayed in step S230 by using a mouse or a touch screen.

In step S250, the fixation lamp setting unit 141 of the control unit 140 sets the turn-on position on the fixation lamp 311 so that the predetermined position on the fundus image acquired in step S240 is close to the imaging position irradiated by the measuring light from the tomographic image acquisition unit 110.

In the present exemplary embodiment, since the fundus image is acquired from a tomographic image, the measuring light projection angle at each position on the fundus image can be acquired at the time of tomographic image capturing.

FIG. 3B illustrates an example of the fixation lamp 311. A panel 316 of the fixation lamp 311 is composed of an 8×10 LED (point light source) matrix 315.

The fixation lamp drive mechanism 310 turns on a light-emitting diode (LED) at a fixation lamp turn-on position (x,y) set by the fixation lamp setting unit 141. FIG. 3B illustrates a state where an LED at a fixation lamp turn-on position (4,3) is turned on.

Figure 4A:
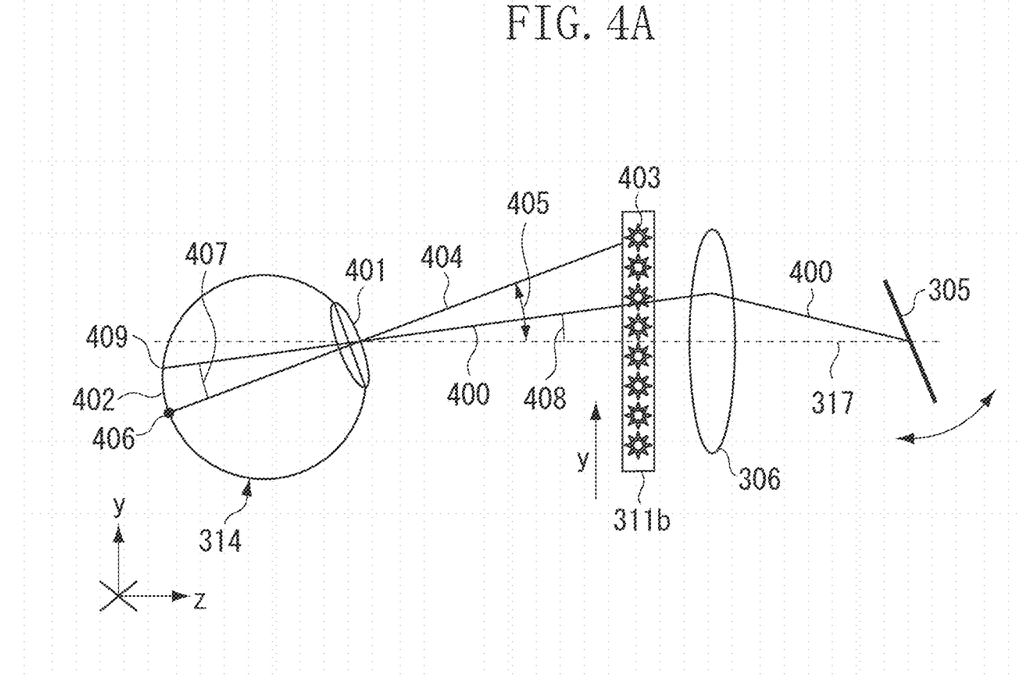
FIGS. 4A to 4C illustrate a relationship among a fixation lamp turn-on position, an imaging portion, and a scanning position according to the first exemplary embodiment.
Figure 4B:
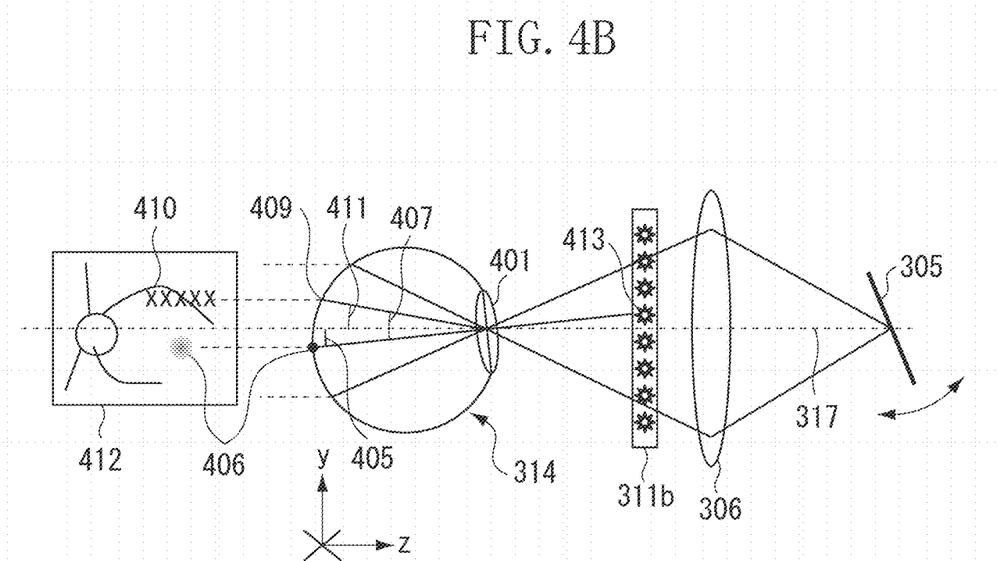
Figure 4C:
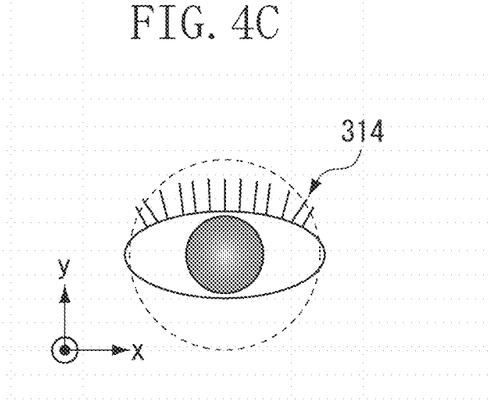

A relationship between the fixation lamp turn-on position and the measuring light projection position will be described below with reference to FIGS. 4A to 4C. FIGS. 4A and 4B illustrate the subject's eye viewed from the lateral side. As illustrated in FIG. 4C, an eyebrow of the subject's eye 314 is positioned at the top thereof.

The vertical direction is referred to as the Y direction. To simplify explanations, fixation lamp turn-on position setting in the Y direction will be described below. Fixation lamp turn-on position setting on the XY plane can be described in a similar way.

The tomographic image acquisition apparatus 110 performs main and sub scanning in the X and Y directions, respectively.

Referring to FIG. 4A, to simplify explanations, it is assumed that an image 311b of the fixation lamp 311 is schematically formed by the lens 312, the half mirror 313, and the objective lens 306.

Measuring light 400 passes through the galvanometer mirror 305 and the objective lens 306 and then advances to the subject's eye 314. Then, the measuring light 400 passes through the cornea and a crystalline lens 401 of the subject's eye 314, and then is projected onto a retina 402 (also referred to as fundus) thereof.

Light from a turned-on LED 403 of the fixation lamp 311 is projected onto the retina 402 via the cornea and the crystalline lens 401 of the subject's eye 314. The light beam from the LED 403 projected onto the retina 402 is referred to as fixation lamp projection light 404. The fixation lamp 311 guides the orientation of the subject's eye 314. When the subject looks at the LED 403 of the fixation lamp 311, the projection position of the fixation lamp 311 corresponds to a macula lutea (yellow spot) 406 of the subject's eye 314. More specifically, the fixation lamp 311 guides the line of sight so that the macula lutea 406 is close to a portion at the fixation lamp projection position on the retina 402.

Further, an angle formed between the fixation lamp projection light 404 and the optical axis 317 of the objective lens 306 is referred to as a fixation lamp projection angle 405. An angle formed between the measuring light 400 and the optical axis 317 is referred to as a measuring light projection angle 408. Further, an angle formed between the measuring light 400 and the fixation lamp projection light 404 is referred to as a fixation deviation angle 407.

A relationship between the fixation lamp turn-on position and the fixation lamp projection angle 405 can be acquired in advance and prepared as a fixation lamp projection angle table.

Figure 5:
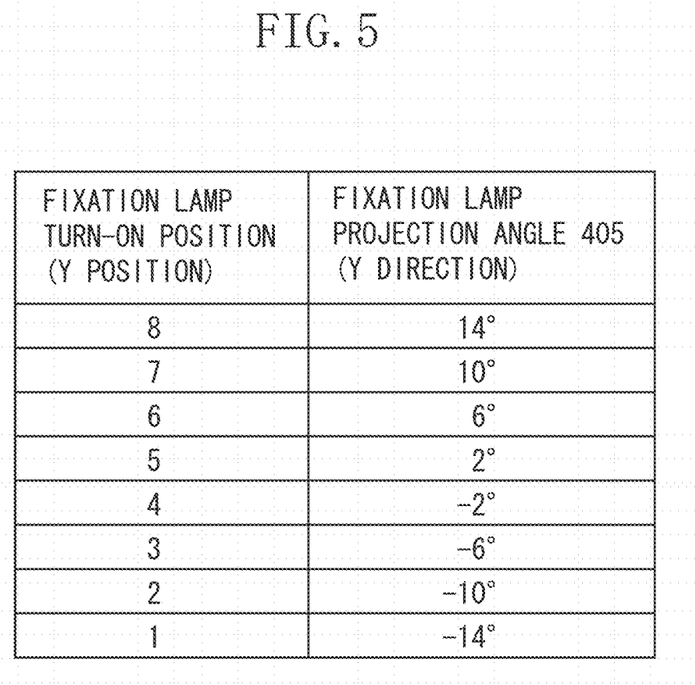
FIG. 5 illustrates an exemplary fixation lamp projection angle table according to the first exemplary embodiment.

FIG. 5 illustrates an exemplary fixation lamp projection angle table. To create the fixation lamp projection angle table, the fixation lamp projection angle 405 is measured in advance by using the tomographic image acquisition apparatus 110. The fixation lamp projection angle 405 can also be calculated by using design values of the components of the tomographic image acquisition unit 110, such as the size of the fixation lamp 311, the arrangement position of the LED 403 of the fixation lamp 311, the lens 312, the half mirror 313, and the objective lens 306.

FIG. 4B illustrates a tomographic image projection image 412 (fundus image) of the retina 402 of the subject's eye 314 fixed by using an initial fixation lamp turn-on position 413. As illustrated in FIG. 4B, when the operator specifies an imaging position 410 on the fundus image 412, an angle RaOca formed between a straight line connecting from an imaging position 409 on the retina 402 to the crystalline lens 401 and the optical axis 317 of the tomographic image acquisition unit 110 is calculated as an angle 411 by using formula (1). The fixation lamp setting unit 141 can obtain the angle 411 as RaOca by using the fundus image 412 and the specified imaging position 410.

$$RpOca = ((\text{Distance to specified position})/(\text{Fundus image size})) \times (\text{Fundus image viewing angle}) \quad (1)$$

The fundus image size denotes the size, in y direction, of the fundus image 412. The distance to specified position denotes the distance, in Y direction, from the center of the fundus image 412 to the specified imaging position 410 in Y direction. The fundus image viewing angle denotes a viewing angle at the time of fundus image capturing.

For example, when the fundus image viewing angle is 30 degrees, the fundus image size is 480 pixels, and the distance to the specified position is 120 pixels, the angle 411 becomes 7.5 degrees.

Further, the fixation lamp setting unit 141 acquires a projection angle FpaL1 at the initial fixation lamp turn-on position 413 from the fixation lamp projection angle table.

From the angle 411 and the initial fixation lamp turn-on position 413, the fixation lamp setting unit 141 acquires Rpa (fixation deviation angle of the macula lutea 406 from the imaging position 409) as the fixation deviation angle 407 by using formula (2).

$$Rpa = RpOca + FpaL1 \quad (2)$$

where FpaL1 denotes an initial fixation lamp projection angle 405.

Then, the fixation lamp setting unit 141 selects, from the fixation lamp projection angle table, a fixation lamp projection angle close to the fixation deviation angle 407 so that the imaging position 409 comes to the vicinity of the optical axis of the tomographic image acquisition unit 110. Then, the fixation lamp setting unit 141 selects the fixation lamp turn-on position of the selected fixation lamp projection angle, and sets the fixation lamp turn-on position.

Fixation lamp turn-on position setting in Y direction has specifically been described above. Fixation lamp x-position setting can also be made in a similar way.

In step S260, the scanning position setting unit 142 of the control unit 140 sets a scanning position so that the specified position is scanned by the measuring light.

The measuring light projection angle 408 can be calculated from the fixation lamp projection angle 405 set in step S250 and the fixation deviation angle 407 of the macula lutea 406 from the imaging position by using formula (3).

$$Ba = Fpa - Rpa \quad (3)$$

where Ba denotes the measuring light projection angle, Fpa denotes the fixation lamp projection angle, and Rpa denotes the fixation deviation angle from the macula lutea.

The scanning position setting unit 142 controls the galvanometer mirror 305 so that the measuring light projection angle 408 becomes Ba. In this case, the scanning position setting unit 142 sets a scanning position within a range narrower than the interval of fixation lamp turn-on positions.

Then, the scanning position setting unit 142 transmits the fixation lamp turn-on position determined in step S250 and the scanning position (measuring light projection angle) determined in step S260 to the tomographic image acquisition unit 110 and the storage unit 130.

With the above-mentioned configuration, acquiring a fundus image of the object under measurement by using the tomographic image capturing apparatus 10 and acquiring an image capturing instruction on the acquired fundus image make it easier to set a fixation lamp turn-on position and a scanning position for capturing an image of the position on the retina corresponding to a specified position on the fundus image.

In the first exemplary embodiment, the operator needs to specify an imaging position on the fundus image. A photographic image capturing apparatus according to a second exemplary embodiment of the present invention acquires an instruction about an imaging portion and position from the operator and controls the fixation lamp turn-on position and scanning position so that the specified imaging position comes to the vicinity of the optical axis of the tomographic image acquisition unit 110.

Since a tomographic image capturing apparatus 10 according to the present exemplary embodiment is configured in a similar way to that in the first exemplary embodiment, explanations will be omitted.

Figure 6:
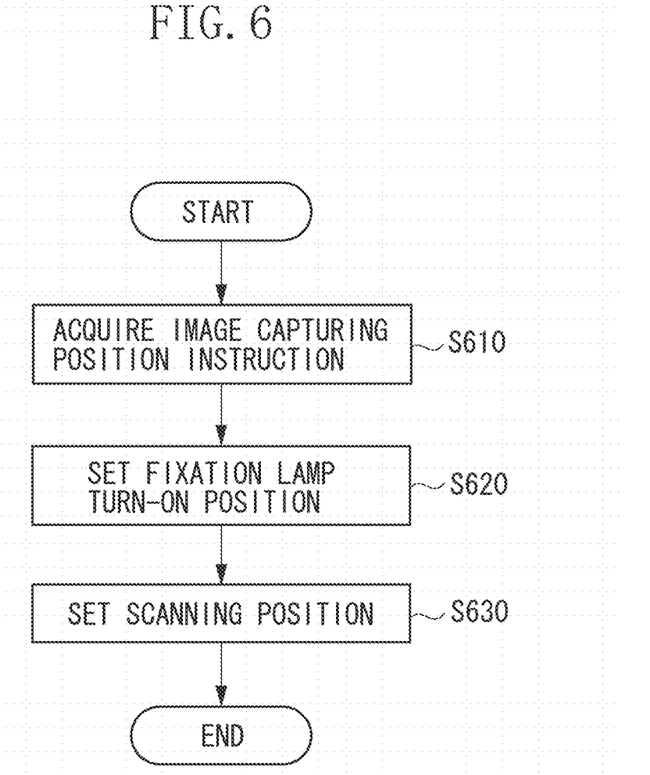
FIG. 6 is a flow chart illustrating processing performed by a tomographic image capturing apparatus according to a second exemplary embodiment of the present invention.

Processing performed by the tomographic image capturing apparatus 10 according to the present exemplary embodiment will be described below with reference to the flow chart in FIG. 6.

In step S610, the instruction acquisition unit 120 acquires a tomographic imaging position instruction about the retina of the subject's eye input by an operator (not illustrated). In the present exemplary embodiment, a position relative to the macula lutea is specified as an imaging position. Although a position relative to the macula lutea will be described below as an example, the imaging position is not limited thereto but may be a portion or a coordinates position in a coordinate system with reference to the macula lutea and optic disc. This instruction is input by the operator via a keyboard or mouse (not illustrated) mounted on the tomographic image capturing apparatus 10. The instruction acquisition unit 120 transmits the acquired instruction to the control unit 140.

In step S620, the fixation lamp setting unit 141 of the control unit 140 sets a fixation lamp turn-on position so that the imaging position specified in the instruction acquired in step S610 comes to the vicinity of the optical axis of the tomographic image acquisition unit 110.

Suppose that the imaging position specified in the instruction acquired in step S610 is 12 degrees in the Y direction of the macula lutea. As seen in FIG. 4A, the fixation deviation angle 407 (angular distance from the macula lutea) formed between the straight line connecting from the imaging position 409 on the retina 402 to the crystalline lens 401 and the straight line connecting from the macula lutea 406 to the crystalline lens 401 becomes 12 degrees. It is necessary to set a fixation lamp turn-on position having a fixation lamp projection angle 405 closest to the fixation deviation angle 407 so that the imaging position 409 on the retina comes to the vicinity of the optical axis 317.

Referring to the fixation lamp projection angle table in FIG. 5, fixation lamp turn-on positions 8 and 7 have a fixation lamp projection angle close to 12 degrees. Here, the fixation lamp turn-on position 7 is selected.

Fixation lamp y-position setting has specifically been described above. Fixation lamp x-position setting can also be made in a similar way.

In step S630, the scanning position setting unit 142 of the control unit 140 sets a scanning position so that the specified position is scanned by the measuring light.

The position of the macula lutea 406 on the retina is determined by turning on the fixation lamp turn-on position set in step S620. The measuring light projection angle 408 can be calculated from a fixation lamp turn-on position Fpa and an angular distance from the macula lutea, Rpa, by using formula (3) in step S260.

In the present exemplary embodiment, from the retina measurement position, since the angular distance from the macula lutea, Rpa, is 12 degrees and the fixation lamp turn-on position Fpa is 10 degrees, the measuring light projection angle Ba is 2 degrees, as seen in FIG. 5.

Since the tomographic image capturing apparatus 10 performs main scanning of the measuring light at the position of the measuring light projection angle in the Y direction, the sub scanning position is assumed to be identical to the measuring light projection angle.

Further, the control unit 140 transmits the fixation lamp turn-on position determined in step S620 and the scanning position (measuring light projection angle) determined in step S630 to the tomographic image acquisition unit 110 and the storage unit 130.

According to the above-mentioned configuration, specifying a specific position on the retina of the object under measurement by using the tomographic image capturing apparatus 10 makes it easier to set a fixation lamp turn-on position and a scanning position.

In the above-described first and second exemplary embodiments, when the operator issues an instruction about an imaging position on the retina (eye), the fixation lamp turn-on position and the scanning position are set in response to the imaging position instruction. In a third exemplary embodiment of the present invention, even if the operator continuously changes the scanning position on a tomographic image during tomographic image capturing, the fixation lamp turn-on position is controlled so that the imaging position constantly scanned comes to the vicinity of the optical axis of the tomographic image acquisition unit 110, and the scanning position is controlled so that the measuring light of the OCT scans the imaging position on the retina.

Since a tomographic image capturing apparatus 10 according to the third exemplary embodiment is configured in a similar way to that in the first exemplary embodiment, explanations will be omitted.

Figure 7:
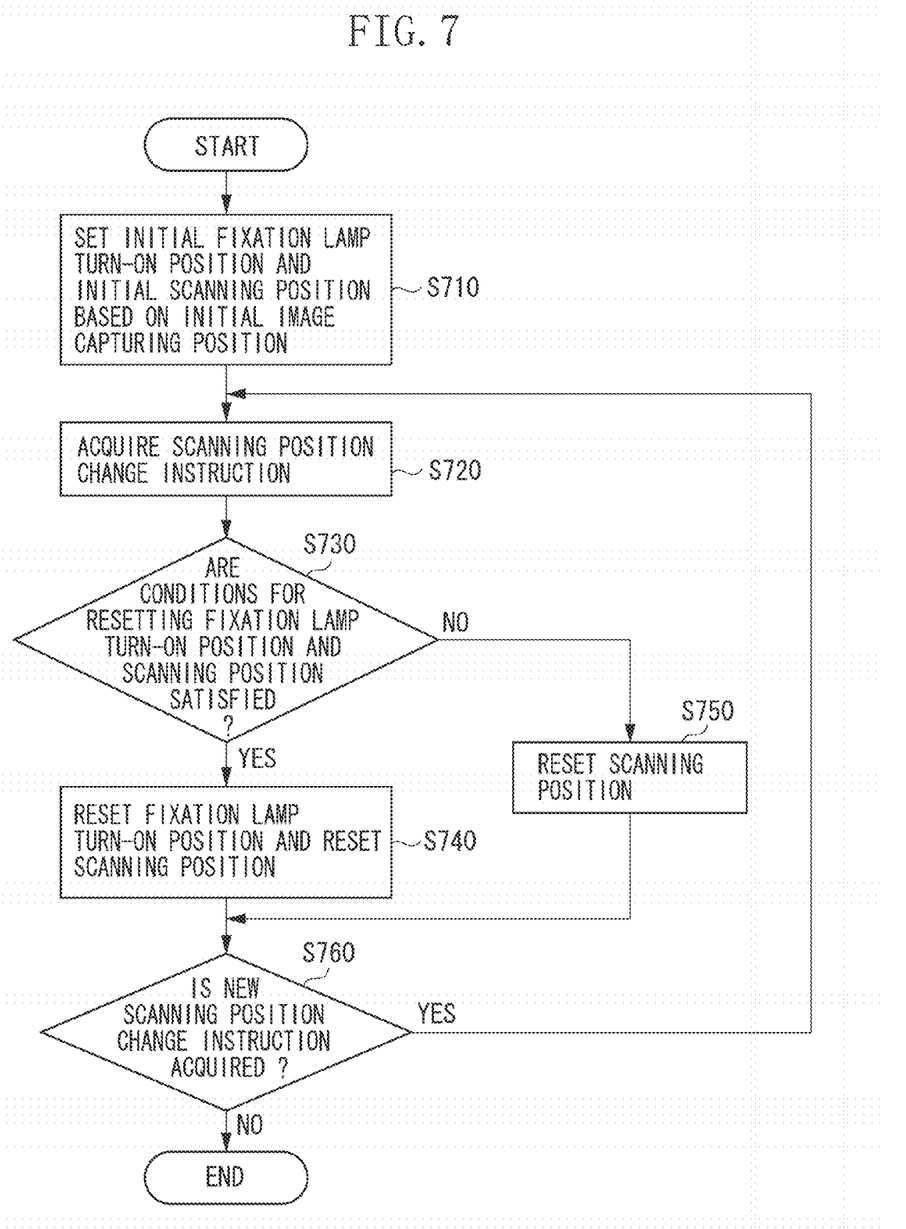
FIG. 7 is a flow chart illustrating processing performed by a tomographic image capturing apparatus according to a third exemplary embodiment of the present invention.

Processing performed by the tomographic image capturing apparatus 10 according to the present exemplary embodiment will be described below with reference to the flow chart in FIG. 7.

In step S710, the control unit 140 determines an initial fixation lamp turn-on position and an initial scanning position. Similarly to the first exemplary embodiment, since a fixation lamp turn-on position and a scanning position are determined in response to the imaging position instruction from the operator, explanations will be omitted. Alternatively, a default fixation lamp turn-on position and scanning position may be predetermined.

The control unit 140 transmits the initial fixation lamp turn-on position and the initial scanning position set in step S710 to the tomographic image acquisition unit 110 and the storage unit 130.

In step S720, the instruction acquisition unit 120 acquires a scanning position change instruction from the operator. This instruction is input by the operator via a mouse, a joy stick, or other input devices (not illustrated) mounted on the tomographic image capturing apparatus 10. The instruction acquisition unit 120 transmits the acquired instruction to the control unit 140.

In step S730, the control unit 140 determines whether conditions for setting the fixation lamp turn-on position and scanning position are satisfied, in response to the scanning position change instruction acquired from the operator in step S720.

First of all, in response to the scanning position change instruction issued by the operator in step S720, the control unit 140 calculates a changed scanning position. The changed scanning position is referred to as temporary scanning position. Referring to FIG. 4A, changing the scanning position will result in a change in the measuring light projection angle 408. The measuring light projection angle 408 increases or decreases in response to the operator's instruction. The measuring light projection angle 408 for the temporary scanning position is represented by Ba'.

The conditions for setting the fixation lamp turn-on position and scanning position include a determination whether there is any fixation lamp turn-on position with which the imaging position on the retina can come closer to the optical axis of the tomographic image acquisition unit 110 as a result of changing the scanning position or the measurement projection angle Ba.

When the fixation deviation angle 407 from the macula lutea after scanning position change is represented by Rpa', Rpa' is calculated by using formula (4).

$$Rpa' = Fpa - Ba' \qquad (4)$$

where Fpa denotes the fixation lamp projection angle.

Then, a fixation lamp projection angle close to Rpa' is selected from the fixation lamp projection angle table, and a fixation lamp turn-on position corresponding to the selected fixation lamp projection angle is selected. When the selected fixation lamp turn-on position is different from the fixation lamp turn-on position stored in the storage unit 130 (YES in step S730), the conditions in step S730 are satisfied, and the processing then proceeds to step S740. Otherwise, when the fixation lamp turn-on position stored in the storage unit 130 is close to the selected fixation lamp turn-on position (NO in step S730), the processing proceeds to step S750.

In step S740, the control unit 140 sets the scanning position and the fixation lamp turn-on position by using the fixation lamp position and the measuring light projection angle Ba' after scanning position change.

First, when the fixation lamp position is changed, the control unit 140 recalculates the measuring light projection angle Ba by using formula (3) in step S260. In formula (3), however, Rpa is replaced by Rpa', and Fpa is the projection angle of the fixation lamp position after scanning position change determined in step S730.

The control unit 140 transmits the fixation lamp turn-on position determined in step S730 and the scanning position (measuring light projection angle) determined in step S740 to the tomographic image acquisition unit 110 and the storage unit 130.

In step S750, the control unit 140 sets a scanning position in response to the operator's instruction without changing the fixation lamp position in step S720, and transmits the set scanning position to the tomographic image acquisition unit 110.

In step S760, the instruction acquisition unit 120 determines whether a new scanning position change instruction is acquired from the operator.

When there is a new instruction (YES in step S760), the processing returns to step S720.

Otherwise, when there is no new instruction (NO in step S760), the processing ends.

The conditions used in step S730 have been described as the conditions that the imaging position is close to the optical axis of the tomographic image acquisition unit 110. However, it is also possible to apply other conditions, for example, a change in distance of the fixation lamp turn-on position after scanning position change, or a condition that the optical axis comes to between an imaging position and a target position.

According to the above-described configuration, the operator can change the fixation lamp turn-on position and the scanning position by simply changing the scanning position in a continuous way.

The present invention is not limited to the above-mentioned exemplary embodiments but may be implemented in diverse ways. More specifically, the tomographic image capturing apparatus 10 illustrated in FIG. 1 can be implemented by hardware or a combination of hardware and software. Referring to FIG. 1, each component of the tomographic image capturing apparatus 10 is a circuit or ASIC having a specific function (in the case of hardware) or a module (in the case of software). When each component is implemented entirely by software, it may be a module operating on a general-purpose personal computer (PC).

While the present invention has been described with reference to exemplary embodiments, it is to be understood that the invention is not limited to the disclosed exemplary embodiments. The scope of the following claims is to be accorded the broadest interpretation so as to encompass all modifications, equivalent structures, and functions.

What is claimed is:

1. An ophthalmic image capturing apparatus comprising:
   a scanning unit configured to scan a fundus of a subject's eye with measuring light;
   a detection unit configured to detect return light from the fundus on which the measuring light is projected via the scanning unit;
   a fixation lamp configured to guide a line of sight of a subject's eye;
   a fixation lamp setting unit configured to set a turn-on position of the fixation lamp so that an acquisition position becomes closer to an optical axis of an optical path of the measuring light, the acquisition position being for acquiring an image of the fundus based on the detected return light; and
   a control unit configured to control the scanning unit so that, in a case where the fixation lamp is turned on in the set turn-on position, a scanning position to be scanned with the measuring light by the scanning unit becomes closer to the acquisition position.

2. The ophthalmic imaging apparatus according to claim 1, further comprising a scanning position setting unit configured to set the scanning position using information about the acquisition position and the set turn-on position so that the scanning position becomes closer to the acquisition position,
   wherein the control unit controls the scanning unit so as to scan the set scanning position with the measuring light.

3. The ophthalmic imaging apparatus according to claim 2, wherein the scanning position setting unit sets the scanning position at an interval narrower than an interval for turn-on positions of the fixation lamp.

4. The ophthalmic imaging apparatus according to claim 1 further comprising:
   a fundus image acquisition unit configured to acquire a fundus image of the subject's eye; and
   a display control unit configured to control a display unit to display the fundus image;
   wherein the acquisition position is set on the displayed fundus image according to an instruction from an operator.

5. The ophthalmic imaging apparatus according to claim 4,
   wherein the detection unit detects composite light obtained by combining the return light from the fundus on which the measuring light is projected via the scanning unit and reference light corresponding to the measuring light,
   wherein the fundus image is a tomographic image of the fundus, and
   wherein the fundus image acquisition unit acquires, as the fundus image, a projection image obtained based on the detected composite light.

6. The ophthalmic imaging apparatus according to claim 1,
wherein the detection unit detects composite light obtained by combining the return light from the fundus on which the measuring light is projected via the scanning unit and reference light corresponding to the measuring light, and
wherein the fundus image is a tomographic image of the fundus.

7. A method for controlling an ophthalmic imaging apparatus comprising:
a scanning unit configured to scan a fundus of a subject's eye with measuring light;
a detection unit configured to detect return light from the fundus on which the measuring light is projected via the scanning unit; and
a fixation lamp configured to guide a line of sight of the subject's eye;
the method comprising:
setting a turn-on position of the fixation lamp so that an acquisition position becomes closer to an optical axis of an optical path of the measuring light, the acquisition position being for acquiring an image of the fundus based on the detected return light; and
controlling the scanning unit so that, in a case where the fixation lamp is turned on in the set turn-on position, a scanning position to be scanned with the measuring light by the scanning unit becomes closer to the acquisition position.

8. The method according to claim 7, further comprising setting the scanning position using information about the acquisition position and the set turn-on position so that the scanning position becomes closer to the acquisition position,
wherein the scanning unit is controlled so as to scan the set scanning position with the measuring light.

9. The method according to claim 8, wherein the scanning position is set at an interval narrower than an interval for turn-on positions of the fixation lamp.

10. The method according to claim 7, further comprising:
acquiring a fundus image of the subject's eye;
displaying the fundus image; and
setting the acquisition position on the displayed fundus image according to an instruction from an operator.

11. The method according to claim 10,
wherein composite light obtained by combining the return light from the fundus on which the measuring light is projected via the scanning unit and reference light corresponding to the measuring light is detected by the detection unit,
wherein the fundus image is a tomographic image of the fundus, and
wherein a projection image obtained based on the detected composite light is acquired as the fundus image in the acquiring.

12. The method according to claim 7,
wherein composite light obtained by combining the return light from the fundus on which the measuring light is projected via the scanning unit and reference light corresponding to the measuring light is detected by the detection unit, and
wherein the fundus image is a tomographic image of the fundus.

13. A non-transitory computer-readable storage medium storing a program for causing a computer to perform a method for controlling an ophthalmic imaging apparatus, the ophthalmic imaging apparatus including a scanning unit configured to scan a fundus of a subject's eye with measuring light, a detection unit configured to detect return light from the fundus on which the measuring light is projected via the scanning unit, and a fixation lamp configured to guide a line of sight of the subject's eye, the method comprising:
setting a turn-on position of the fixation lamp so that an acquisition position becomes closer to an optical axis of an optical path of the measuring light, the acquisition position being for acquiring an image of the fundus based on the detected return light; and
controlling the scanning unit so that, in a case where the fixation lamp is turned on in the set turn-on position, a scanning position to be scanned with the measuring light by the scanning unit becomes closer to the acquisition position.

* * * * *